United States Patent
Hobbs et al.

(10) Patent No.: US 8,043,847 B2
(45) Date of Patent: Oct. 25, 2011

(54) SYSTEM INCLUDING A TUNABLE LIGHT AND METHOD FOR USING SAME

(75) Inventors: Ray Hobbs, Avondale, AZ (US); David Haberman, Delroy Beach, FL (US)

(73) Assignee: Arizona Public Service Company, Phoenix, AZ (US)

( * ) Notice: Subject to any disclaimer, the term of this patent is extended or adjusted under 35 U.S.C. 154(b) by 1118 days.

(21) Appl. No.: 11/627,501

(22) Filed: Jan. 26, 2007

(65) Prior Publication Data

US 2008/0182325 A1    Jul. 31, 2008

(51) Int. Cl.
*C12M 1/42* (2006.01)
*C12M 1/107* (2006.01)

(52) U.S. Cl. ............... 435/292.1; 435/300.1; 47/1.4; 362/159

(58) Field of Classification Search .............. 435/292.1, 435/300.1; 362/159; 47/1.4
See application file for complete search history.

(56) References Cited

U.S. PATENT DOCUMENTS

| | | |
|---|---|---|
| 2003/0176278 A1 | 9/2003 | Wickham et al. |
| 2005/0239182 A1 | 10/2005 | Berzin |
| 2007/0117195 A1* | 5/2007 | Warner et al. ............... 435/161 |

FOREIGN PATENT DOCUMENTS

| | | |
|---|---|---|
| DE | 202004009310 U1 | 9/2004 |
| WO | WO03064925 A | 8/2003 |
| WO | WO03094598 A | 11/2003 |
| WO | WO2005001104 A | 1/2005 |

OTHER PUBLICATIONS

Stuecker et al. "Advanced Support Structures for Enhanced Catalytic Activity" Ind. Eng. Chem. Res. vol. 43 (2004), pp. 51-55.*
International Search Report and Written Opinion from PCT/US07/84916 dated Aug. 7, 2008.

* cited by examiner

*Primary Examiner* — William H Beisner
(74) *Attorney, Agent, or Firm* — Snell & Wilmer L.L.P.

(57) ABSTRACT

The present invention provides a system and method for providing light, which can be used to promote growth of biological material. The light includes a ceramic core, including a catalyst and a containment vessel. Light forms as fuel is ignited within the containment vessel. Use of the ceramic core increases the efficiency of the light are reduces undesired gas emissions from the light.

9 Claims, 4 Drawing Sheets

SYSTEM INCLUDING A TUNABLE LIGHT AND METHOD FOR USING SAME

FIELD OF INVENTION

The present invention generally relates systems and methods including a tunable light. More particularly, the invention relates to systems and methods including a ceramic light source, which can be used to promote growth of biological material.

BACKGROUND OF THE INVENTION

Natural sunlight provides energy to many biological organisms. For example, plants, including algae, use light in photosynthesis processes to produce sugar and oxygen.

Often times, it is desirable to add additional, artificial light to biological material to further facilitate the growth of the material. For example, incandescent, fluorescent, or a combination of such light is often applied to plants, where natural sunlight is unavailable or insufficient for the desired growth. Although such lights work relatively well in certain applications, incandescent and fluorescent lights often have set wavelengths of emitted lights, and the lights are relatively inefficient at converting energy (e.g., electricity) into light. Accordingly, improved systems and methods for providing light to biological material are desired.

One area of particular interest in which biological material, such as algae, is used and where application of artificial light may be particularly desirable is in bioreactors, which use biological material to convert $CO_x$ (typically $CO_2$) to maintainable carbon and oxygen.

Carbon maintenance and carbon sequestration are desirable for several reasons. For example, global warming and other environmental changes are thought to be affected by the increased amount of carbon dioxide ($CO_2$), methane ($CH_4$), nitrogen oxides ($NiO_x$) and other greenhouse gasses in the atmosphere. Thus, it is thought that such environmental changes can be reduced and/or reversed by reducing emission of greenhouse gasses, and in particular, carbon-based gasses.

Fossil fuel power plants, such as coal plants, are thought to generate a substantial portion of the greenhouse gas emission. Thus, considerable effort has been made to reduce greenhouse gas emissions from such plants. Increasing fossil-fuel plant efficiency, reducing use of fossil-fuel plants, using fuels with less carbon in power plants are some of the approaches used to reduce carbon emissions. However, as the world population increases and demand for energy increases, the overall emission from fossil-fuel plants is likely to increase. Thus, systems, methods, and devices, which reduce overall carbon emission and other harmful gasses, e.g., from fossil fuel plants, and/or that make use of such gasses are desirable.

SUMMARY OF THE INVENTION

The present invention provides improved systems and methods including a tunable light source, which can be used for providing light to biological material. While the ways in which the present invention addresses the various drawbacks of the prior are discussed in greater detail below, in general, the invention provides systems and methods having efficient, non-electrical lights, which can be tuned to desired light wavelengths. Such systems and methods can be used to facilitate growth of biological material in an efficient manner.

In accordance with various embodiments of the invention, a system includes a light source having catalytically doped hexaaluminate ceramic material. The inclusion of the ceramic material reduces $NO_x$ and $CO_x$ emission, compared to traditional combustion-based light sources, and provides a tunable light source, in which the wavelengths of light emitted from the light source can be manipulated by adjusting factors such as input fuel, the ceramic material, and operating conditions. Light from the source can be applied to a variety of biological material, such as algae and other plants to facilitate growth of the material. Moreover, the wavelength of the light can be tuned for desired results, such as increased growth of certain material, increased growth of certain material relative to other material, and possibly retarding the growth of nonsynergistic plants and organisms.

In accordance with one embodiment of the invention, a bioreactor system includes a tunable light source, a bioreactor vessel, and biological material within the vessel. The tunable light provides energy to the biological material and generates COx during the production of the light. The biological material converts product gasses from the light source (e.g., CO and $CO_2$), and optionally other gasses, to oxygen and carbon or hydrocarbons, which can be harvested and/or used as fuel—e.g., in a power plant.

In accordance with another embodiment of the invention, a system for using biological material in the production of electricity and management of carbon includes a first reactor to hydrogenate a carbon fuel source such as coal to form methane, a second reactor to convert methane to electricity (with water and $CO_x$ as byproducts), a third reactor that converts $CO_x$ to $O_2$ and solid hydrocarbons, and an efficient combustion light device, which burns gaseous hydrocarbon fuel—e.g., effluent from the first reactor—to provide light to the third reactor. In accordance with various aspects of this embodiment, the third reactor is a bioreactor and the light is used to supply energy to biological material within the reactor. In accordance with additional aspects of this embodiment, the light provides additional energy to the biological material when natural sunlight is unavailable or is at a less than desired intensity. In accordance with yet further aspects of this embodiment, $CO_x$, produced from the combustion reaction of the light, is sent to the third reactor for conversion of $CO_x$ to $O_2$ and solid hydrocarbons, which can be sequestered, sent back to the first reactor as fuel, or otherwise used. An amount of carbon emitted to the atmosphere during production of electricity from hydrocarbons is thus reduced using the exemplary system.

In accordance with yet another embodiment of the invention, a system for using biological material to produce electricity and maintain carbon includes a first combustion reactor to convert hydrocarbon material to electricity (with water and $CO_x$ as byproducts), a bioreactor to convert the $CO_x$ to solid hydrocarbon material and $O_2$, and a combustion light device to provide energy to the bioreactor and thereby increase the efficiency of the bioreactor.

In accordance with yet another embodiment of the invention, a method of cultivating biological material includes providing biological material, providing a combustion ceramic light proximate the biological material, combusting fuel within the ceramic light to cause the ceramic material to glow and emit light, and applying the light to the biological material.

In accordance with another embodiment of the invention, a method of using biological material to produce electricity and maintain carbon includes providing a combustion reactor to convert hydrocarbon material to electricity (with water and $CO_x$ as byproducts), providing a bioreactor proximate the combustion reactor, providing a combustion ceramic light proximate the bioreactor, feeding $CO_x$ from the combustion reactor to the bioreactor, and, using the bioreactor, converting the $CO_x$ from the combustion reactor to O2 and solid hydrocarbons, which can be sequestered or used as, for example, a fuel source.

BRIEF DESCRIPTION OF THE DRAWINGS

The exemplary embodiments of the present invention will be described in connection with the appended drawing figures in which like numerals denote like elements and.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

The present invention provides a system and method that include a high-efficiency, tunable light, which can be used for promoting growth of biological material. As explained in more detail below, the system and method can be used to maintain and/or sequester carbon in various applications, such as power generation from fossil fuels, and the like.

Figure 1:
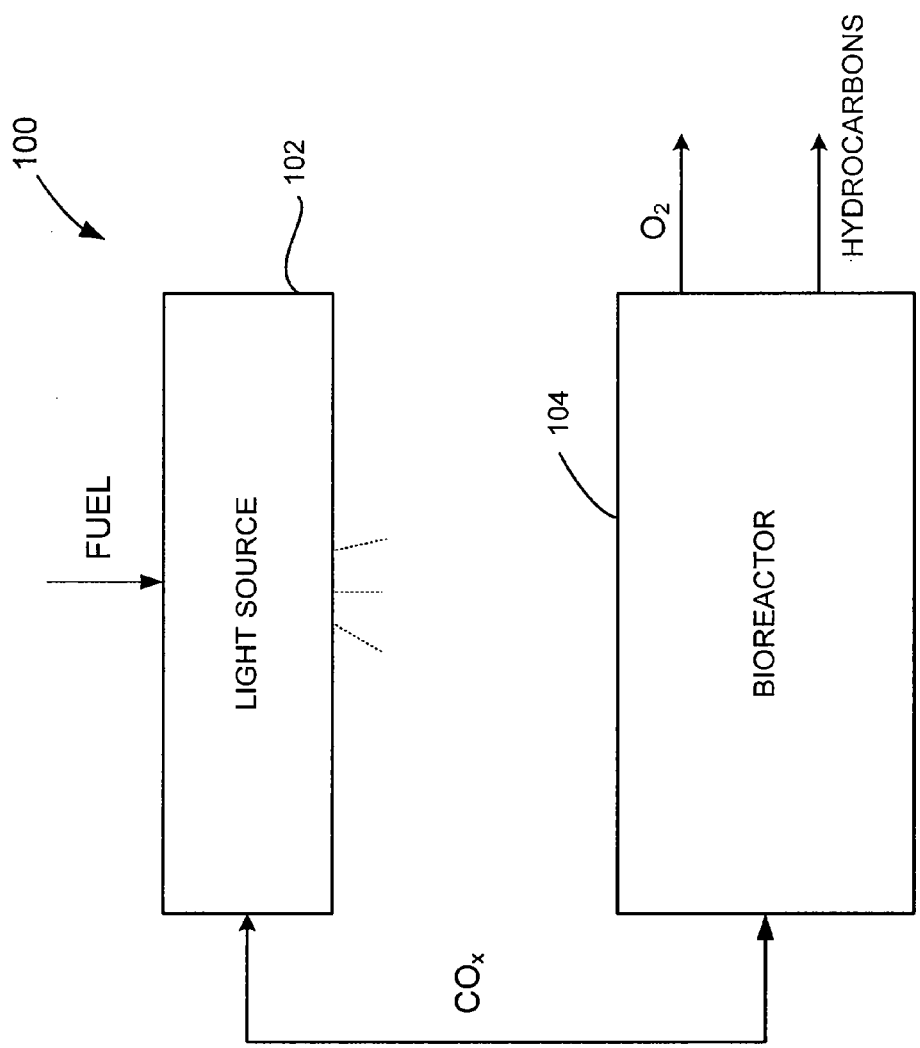
FIG. 1 illustrates a system for facilitating biological growth in accordance with various embodiments of the invention.

FIG. 1 illustrates a system 100 in accordance with various embodiments of the invention. System 100 includes a light source 102 and a bioreactor 104.

Light source 102 is a high-efficiency, tunable, combustion-based light source. As discussed in more detail below, source 102 includes a ceramic core structure, which includes catalytic material to increase the efficiency (conversion of fuel to light) of the light and to decrease undesired emission from source 102. In accordance with various embodiments of the invention, light source 102 is powered by a hydrocarbon fuel (e.g., methane), and $CO_x$ is produced as a byproduct.

Light source 102 may be used to provide light to various biological materials such as plants—e.g., algae. Source 102 may be used to supplement sunlight, to increase an overall amount of light provided to the biological material and/or used to provide light of specific wavelengths. Source 102 may also be used to provide temporary lighting—e.g., for construction and/or road repair. In this case, the light is attached to a retractable pole to facilitate easy movement of source 102.

In accordance with various embodiments of the invention, light source 102 provides light to bioreactor 104 to increase the overall efficiency of reactor 104 and thus use of light 102 in conjunction with bioreactor 104 increases the ability of reactor 104 to absorb $CO_x$ and produce biomass.

Bioreactor 104 may be configured to facilitate growth of a variety of materials. For example, bioreactor 104 may be designed to facilitate growth of biological material, such as various forms of algae, that converts $CO_x$ to oxygen and hydrocarbon material. The hydrocarbon material can be sequestered or used as fuel or other purposes. In accordance with various aspects of this exemplary embodiment, bioreactor 104 includes algae, which converts $CO_x$ (e.g., product from light source 102) to oxygen and hydrocarbon materials such as sugar, starches, ethanol, diesel fuel, and the like.

Figure 2A:
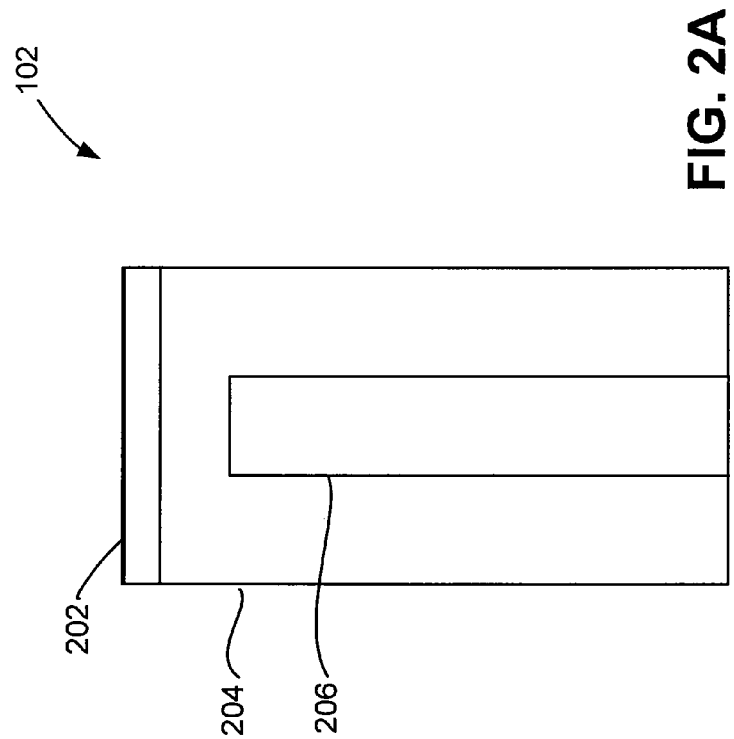
FIGS. 2a and 2b illustrate a ceramic light for use with various embodiments of the invention.
Figure 2B:
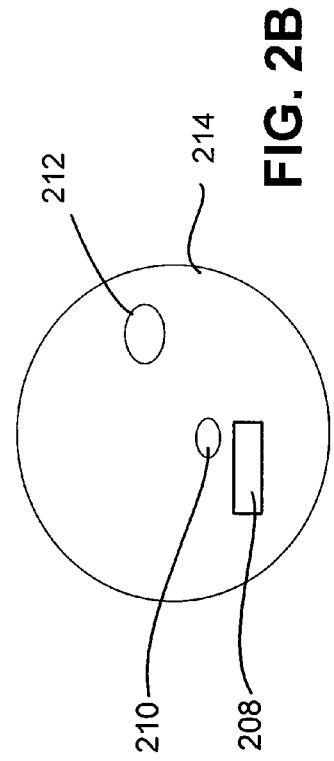

FIGS. 2a and 2b illustrate an exemplary light source 102, for use in connection with various embodiments of the invention, in greater detail. Light source 102 includes a diffusing lens 202, a light-transparent containment vessel 204, a ceramic structure 206, a directional combustor 208, a natural gas input 210, a pressure relief and gas output valve 212, and a vessel endcap 214.

Lens 202 may be integral with or attached to vessel 204. In accordance with one particular aspect of the illustrative embodiment, lens 202 is formed of glass.

Vessel 204 may be formed of any material that transmits light of desired wavelengths, is capable of withstanding the operation temperature of the light, is relatively insulating, and is capable of encapsulating combustion and product gases within light source 106. Exemplary materials suitable for vessel 204 include glass, quartz, and the like.

Ceramic structure 206 is formed of a material that becomes highly emissive in the presence of combustion of hydrocarbon material—e.g., methane—at its product gasses. In accordance with various aspects of the exemplary embodiment, structure 206 is formed of metal element (e.g., palladium, platinum) doped hexaaluminate ceramic material. Doping the hexaaluminate material with catalysts such as platinum or palladium is advantageous, because such catalysts facilitate high efficiency, low emission combustion of hydrocarbon materials, such as methane. For example, a doped hexaaluminate light source in accordance with one exemplary aspect is about 90% efficient and can significantly reduce or eliminate $NO_x$ emissions typical of combustion light sources, since the combustion temperature can be below the temperature at which nitrogen oxides form.

In operation, fuel such as methane is fed to light source 106. The fuel is regulated to a low pressure using gas input valve 210, which can be remotely controlled. As the gas passes through valve 210, the gas is ignited by controllable, directional combustor 208, such that the combustion is directed into the center of the ceramic structure. The hot gas flows into tubular ceramic structure 206, which is energized by the hot gas to glow brightly. Small amounts of the combustion fuel combine with the combustion gas products, mostly $CO_2$ and CO in the pressurized space surrounding the ceramic structure. The light produced from the glowing ceramic structure diffuses through the transparent containment vessel and through lens 202. The spectrum of the emitted light is a function of the chemistry of the ceramic structure 206 (e.g., the catalyst material), the fuel, the ambient pressure in the vessel, all of which are controllable. The combustion gas products are released in a regulated fashion through valve 212, to feed downstream bioreactor 104. In the event of any overpressure, the gas output valve is configured to dump the combustion gas into the bioreactor to quench the heat. The pressure relief valve is coupled to an override switch to kill the ignition of the input gas. Pressure relief valve 212 is tied to an input valve emergency shutoff to stop fuel from entering the vessel in the event of an overpressure.

The rate of fuel gas (e.g., $CH_4$) introduction will effect both the wavelength and frequency of light spectra produced. The combustion efficiency measured as the ratio of heat energy to light energy is a function of the amount of fuel available, the pressure level in the vessel, the turbulence in the vessel, the rate of $CO_2$ removal and the distribution of the fuel within the ceramic structure inside the vessel. This combustion efficiency calculation derives the light energy (wattage). Spectra emission is tuned by control of the factors that effect combustion efficiency. This control is accomplished by fixed design features in concert with tunable operation modes such as fuel flow valves and pressure relief valves.

Figure 3:
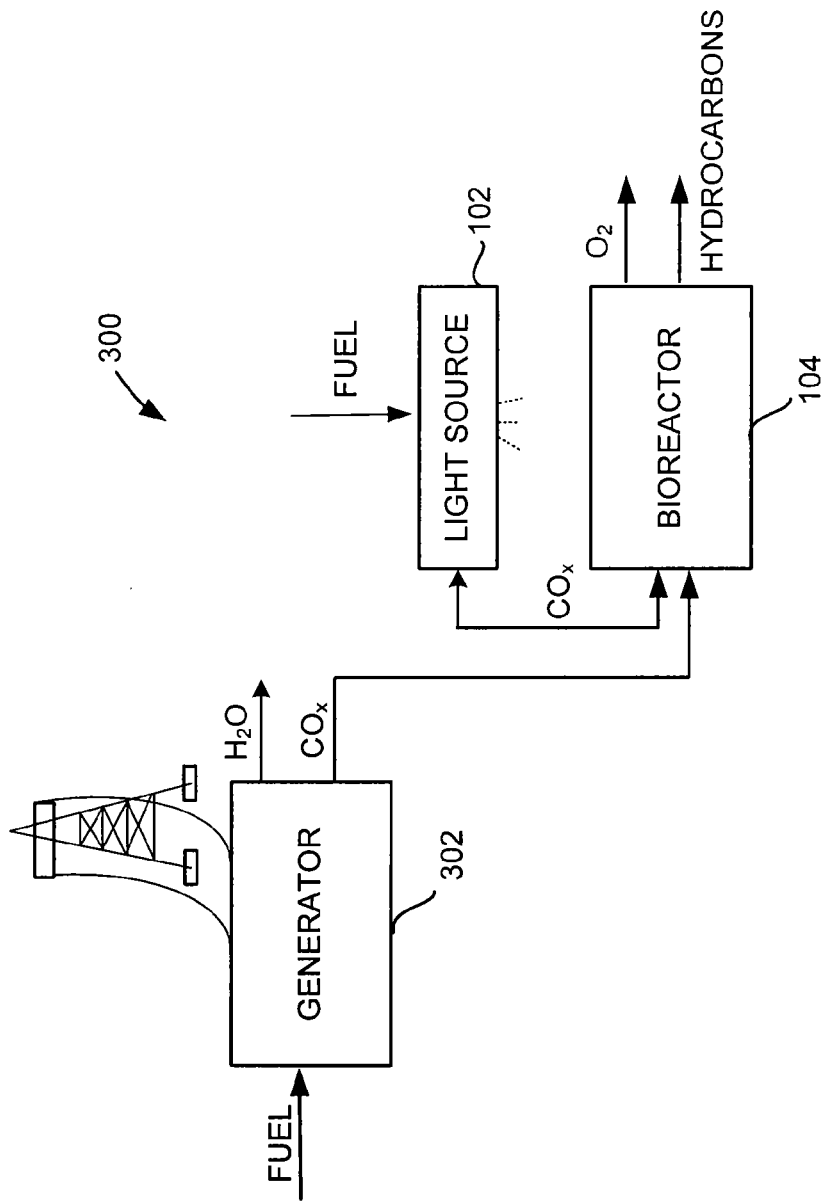
FIG. 3 illustrates a system for producing light and maintaining carbon.

FIG. 3 illustrates a system 300, which includes light source 102, bioreactor 104, and a power generator 302. Generator 302 may include any generator that burns a hydrocarbon fuel to generate electricity. In accordance with one exemplary aspect of this embodiment, generator 302 is a methane power generator, which combusts methane with air to generate electrical power. The methane may be derived from a variety of sources, such as animal sources, underground sources, or, as described in more detail below, from hydrogenated coal. As the methane is combusted, water and $CO_x$ (typically mostly $CO_2$) are formed.

In accordance with various embodiments of the invention, $CO_x$ produced by generator 302 is fed to bioreactor 104 to maintain or sequester the carbon. And, in accordance with additional embodiments, the fuel used to power generator 302 (e.g., methane) is the same fuel used to power light source 102.

Figure 4:
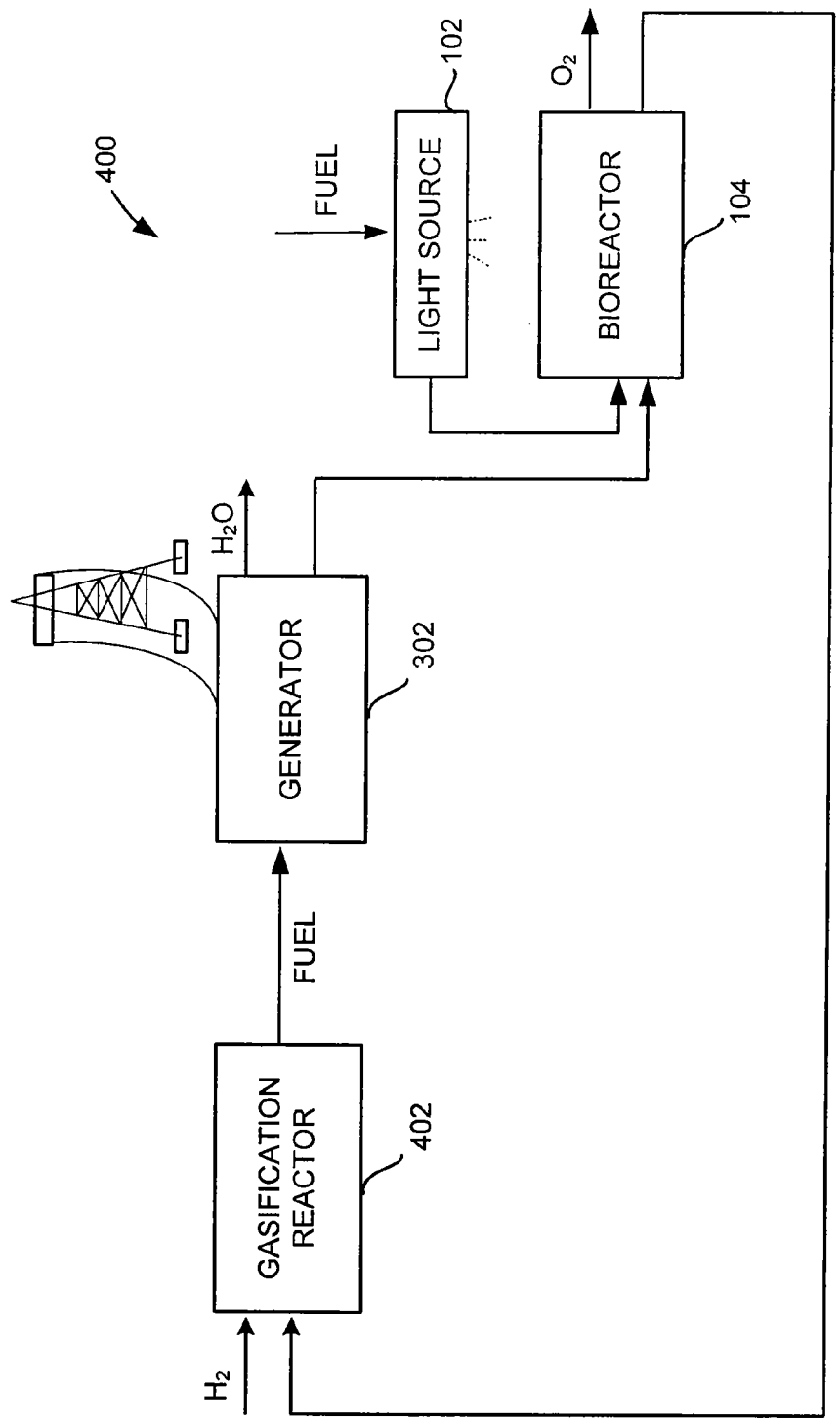
FIG. 4 illustrates a system, including a ceramic light, for producing energy and maintaining carbon.

FIG. 4 illustrates another system 400 in accordance with various exemplary embodiments of the invention. System 400 is similar to system 300, except system 400 includes an additional gasification reactor 402, which feeds fuel to generator 302 and optionally receives at least some of the operating fuel from bioreactor 104.

Gasification reactor 402 can include any reactor that produces fuel suitable for generator 302. In this case, hydrogen and coal are reacted to form methane. In accordance with various embodiments, the methane is fed to reactor 302 and reacted with air to produce water and $CO_x$. The $CO_x$ is then fed to bioreactor 104.

Although exemplary embodiments of the present invention are set forth herein, it should be appreciated that the invention is not so limited. For example, although the systems are described in connection with various bioreactors, the invention is not so limited. Various modifications, variations, and enhancements of the system and method set forth herein may be made without departing from the spirit and scope of the present invention as set forth in the following claims and their equivalents.

We claim:

1. A system for producing electricity and maintaining carbon, the system comprising:
 a gasification reactor, which generates a fuel;
 a generator coupled to the gasification reactor, wherein the generator converts the fuel into electricity and $CO_x$;
 a bioreactor coupled to the generator, wherein the bioreactor receives $CO_x$ from the generator and converts the $CO_x$ to $O_2$ and hydrocarbon; and
 a tunable light source coupled to the gasification reactor and the bioreactor, the tunable light source having a vessel and a ceramic core comprising emissive material, wherein combustion of the fuel is directed into the center of the ceramic core to cause the core to glow and form a spectrum of light, comprising wavelengths and frequencies, the wavelengths and frequencies tunable by varying a parameter selected from the group consisting of fuel, pressure in the vessel, and rate of fuel gas to the tunable light, the tunable light source proximate the bioreactor, wherein the tunable light source provides light to the bioreactor, and wherein effluent from the tunable light is fed to the bioreactor.

2. The system for producing electricity and maintaining carbon of claim 1, wherein the bioreactor includes algae.

3. The system for producing electricity and maintaining carbon of claim 1, wherein the ceramic core comprises a metal selected from the group consisting of palladium and platinum.

4. The system for producing electricity and maintaining carbon of claim 1, wherein the light source comprises hexaaluminate.

5. The system for producing electricity and maintaining carbon of claim 1, wherein the light source comprises catalyst material.

6. The system for producing electricity and maintaining carbon of claim 1, wherein the light source comprises material selected from the group consisting of metal elements.

7. The system for producing electricity and maintaining carbon of claim 1, wherein the gasification reactor generates hydrogenated fuel.

8. The system for producing electricity and maintaining carbon of claim 1, wherein the fuel is methane.

9. The system for producing electricity and maintaining carbon of claim 1, wherein the bioreactor is coupled to the gasification reactor.

* * * * *